United States Patent [19]  
Burow, Jr. et al.

[11] 4,421,546  
[45] Dec. 20, 1983

[54] AQUATIC METHOD

[75] Inventors: Kenneth W. Burow, Jr., Indianapolis; Roger L. St. Clair, Greenfield, both of Ind.

[73] Assignee: Eli Lilly and Company, Indianapolis, Ind.

[21] Appl. No.: 403,209

[22] Filed: Jul. 29, 1982

Related U.S. Application Data

[62] Division of Ser. No. 334,410, Dec. 24, 1981, Pat. No. 4,354,030.

[51] Int. Cl.$^3$ ............................................. A01N 37/100
[52] U.S. Cl. ........................................................ 71/66
[58] Field of Search ............................................. 71/66

[56] References Cited

U.S. PATENT DOCUMENTS

| | | | |
|---|---|---|---|
| 3,498,998 | 3/1970 | Hughes et al. | 71/66 |
| 3,564,606 | 2/1971 | Breuer | 71/66 |
| 3,573,317 | 3/1971 | Smith | 71/66 |
| 3,667,930 | 6/1972 | Breuer | 71/66 |
| 4,268,679 | 5/1981 | Lavanish | 548/247 |
| 4,302,239 | 11/1981 | Lavanish | 71/88 |
| 4,318,730 | 3/1982 | Moni | 71/66 |

FOREIGN PATENT DOCUMENTS 38-3697  4/1963  Japan ..................... 71/92

OTHER PUBLICATIONS

Gagliardi et al., "2-Imidazolidinones", *Chem. Abst.* 58, 1467b, (1963).

Gagliardi et al., "Polyalkylated Monoureins", *Chem. Abst.* 63, 18098(c), (1965).

*Primary Examiner*—Paul J. Killos
*Attorney, Agent, or Firm*—Charles W. Ashbrook; Arthur R. Whale

[57] ABSTRACT

Isoxazolylimidazclidinones are useful in the control of aquatic vegetation.

24 Claims, No Drawings

AQUATIC METHOD

This application is a division, of application Ser. No. 334,410, filed 12/24/81, U.S. Pat. No. 4,354,030.

BACKGROUND OF THE INVENTION

The use of chemicals in agriculture has become a common practice throughout the world. Practically all crops that are grown for human consumption are grown in the presence of chemicals. Terrestrial herbicides are routinely employed to control unwanted grassy and broadleaf weeds in desirable food crops such as corn and soybeans.

While there are numerous chemical agents currently available that are effective as selective terrestrial herbicides, few agents are available for controlling the growth of aquatic vegetation in water bodies such as lakes, ponds, streams, rivers and the like. Most herbicides that are effective terrestrially are not suitable for use in aquatic environments. This may be due to the fact that the terrestrial herbicides simply will not control the aquatic vegetation, the terrestrial herbicide is not stable in an aquatic environment, or because the toxicity of the terrestrial herbicides render them unfit for use in water containing animal life.

Lavanish, in U.S. Pat. No. 4,268,679, recently reported a series of isoxazolylimidazolidinones that are effective as terrestrial herbicides and are safe for use on corn, soybeans, wheat and the like. We have now discovered that certain isoxazolylimidazolidinones are useful in the control of aquatic vegetation in bodies of water. An object of this invention therefore is to provide an aquatic herbicidal method employing isoxazolylimidazolidinones.

SUMMARY OF THE INVENTION

This invention concerns a method for controlling the growth of vegetation in bodies of water. The invention is more particularly directed to a method for controlling the growth of aquatic plants comprising contacting the plants with an aquatic herbicidally effective amount of an isoxazolylimidazolidinone defined by the formula

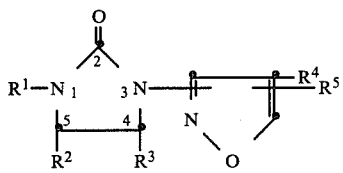

wherein:
$R^1$ is $C_1$–$C_6$ alkyl or allyl;
$R^2$ is hydrogen, $C_1$–$C_6$ alkyl, allyl, or hydroxy;
$R^3$ is hydroxy or halo;
$R^4$ is hydrogen, $C_1$–$C_6$ alkyl, halo, cyano, or nitro;
$R^5$ is $C_1$–$C_6$ alkyl, $C_2$–$C_6$ alkenyl, $C_2$–$C_6$ alkynyl, $C_3$–$C_7$ cycloalkyl, $C_1$–$C_3$ alkyl-$C_3$–$C_7$ cycloalkyl, halo-$C_1$–$C_6$ alkyl, $-R^6-O-R^7$ or $-R^6-S-R^7$, where $R^6$ is $C_1$–$C_6$ alkylene and $R^7$ is $C_1$–$C_6$ alkyl; or $R^5$ is

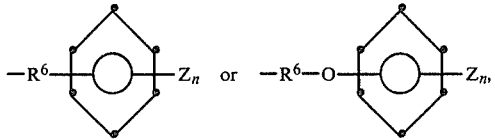

wherein:
Z is nitro, halo, or $R^7$, and n is 0, 1, 2 or provided that $R^2$ is allyl or hydroxy when $R^1$ is alkyl, $R^3$ is hydroxy, and $R^5$ is alkyl, cycloalkyl, alkylcycloalkyl or haloalkyl.

A preferred method of controlling aquatic vegetation employs a compound of the above formula wherein $R^2$ and $R^3$ both are hydroxy.

Another preferred method employs a compound wherein $R^5$ is 1,1-dimethylethyl.

A further embodiment of this invention is an aquatic formulation comprising an isoxazolylimidazolidinone of the above formula and an aquatically-acceptable carrier.

This invention also provides a group of new compounds defined by the formula

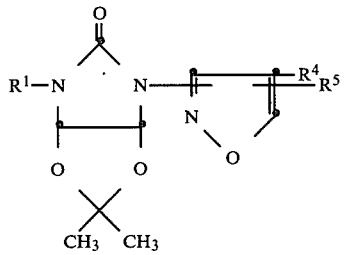

wherein $R^1$, $R^4$ and $R^5$ are as defined above.

DETAILED DESCRIPTION OF THE INVENTION $R^1$ in the above formula defines allyl or a $C_1$–$C_6$ alkyl group. The term "$C_1$–$C_6$ alkyl" means both straight and branched chains having up to six carbon atoms. Typical $C_1$–$C_6$ alkyl groups include methyl, ethyl, isopropyl, n-butyl, 2-methylpentyl, 1,2-dimethylpropyl, and the like. Methyl is preferred for $R^1$.

The term "halo" as used herein means fluoro, chloro, bromo and iodo.

Typical $C_2$–$C_6$ alkenyl groups include 2-propenyl, 2-butenyl, 2-methyl-3-pentenyl, and 5-hexenyl. Common $C_2$–$C_6$ alkynyl groups include 3-hexynyl, 2-propynyl, 2-butynyl, 1-methyl-2-butynyl and the like.

The term "$C_3$–$C_7$ cycloalkyl" includes cyclopropyl, cyclobutyl, cyclopentyl and cycloheptyl. "$C_1$–$C_3$ alkyl-$C_3$–$C_7$-cycloalkyl" means a $C_3$–$C_7$ cycloalkyl group substituted with a $C_1$–$C_3$ alkyl moiety. Examples include 1-ethylcyclohexyl, 1-methylcyclopropyl, and 2-isopropylcyclopentyl.

The term "halo-$C_1$–$C_6$ alkyl" means a $C_1$–$C_6$ alkyl group substituted by one or more halo groups. Trifluoromethyl is a preferred haloalkyl group. Other haloalkyl groups are 2-chloroethyl, 3,4-dibromopentyl, 2-bromo-3-iodohexyl, and the like.

The terms "$-R^6-O-R^7$" and "$-R^6-S-R^7$" refer to groups such as methoxymethyl, 2-ethoxyethyl, 3-isopropylthiopropyl, methylthiomethyl, 6-methylthiohexyl and the like.

Most of the compounds employed in the aquatic method of this invention are disclosed by Lavanish in U.S. Pat. No. 4,268,679. That patent is incorporated herein by reference. As noted therein, isoxazolylimidazolidinones of the above formula wherein $R^2$ is other than hydroxy are prepared by reacting a 3-aminoisoxazole or a 5-aminoisoxazole with phosgene to obtain the corresponding isoxazole isocyanate, reacting the isocyanate with a 2,2-dialkoxyethylamine to provide a urea intermediate, and then cyclizing the urea. This overall scheme is depicted below.

wherein $R^1$, $R^4$ and $R^5$ are as defined above, $R^2$ is other than hydroxy, and "alk" is lower alkyl such as methyl or ethyl.

Isoxazolylimidazolidinones having the above general formula wherein $R^2$ is hydroxy, which are employed in a preferred embodiment of this invention, are prepared by reacting a 3-aminoisoxazole or a 5-aminoisoxazole with an isocyanate to form an isoxazolylurea derivative, and then reacting the isoxazolylurea with glyoxal to form the isoxazolyl-4,5-dihydroxyimidazolidinone. This reaction sequence is depicted by the following scheme;

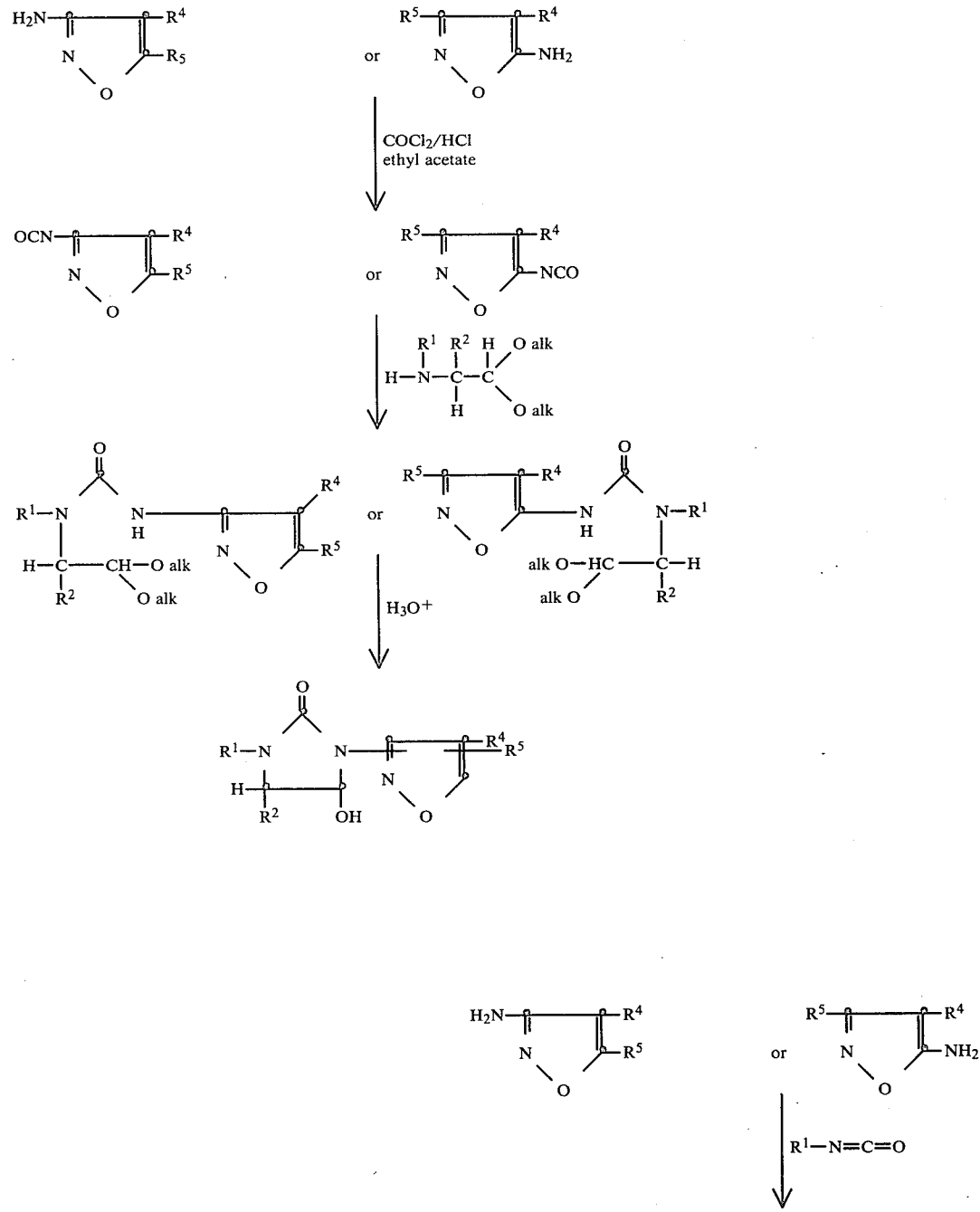

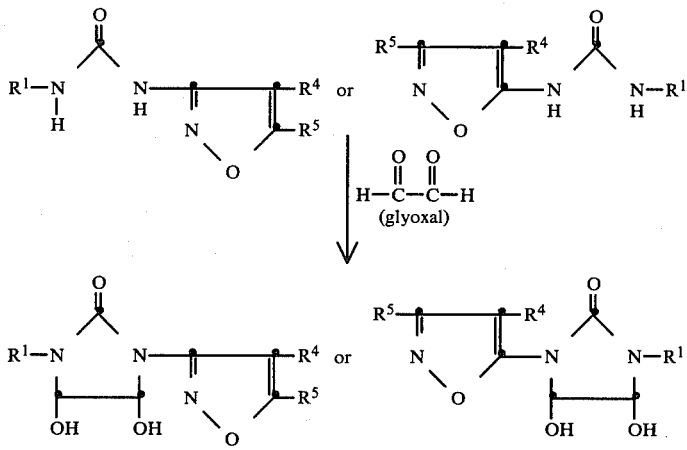

The isoxazolyl-4,5-dihydroxyimidazolidinones wherein the hydroxy groups are cis are valuable in the control of aquatic weeds according to this invention, and also serve as intermediates in the synthesis of the isoxazolylimidazolidinone acetonides that are provided as a further embodiment of the invention. The acetonides can be prepared by reaction of the cis-4,5-dihydroxy imidazolidinones with acetone in the presence of a dehydrating agent and dilute mineral acid as follows:

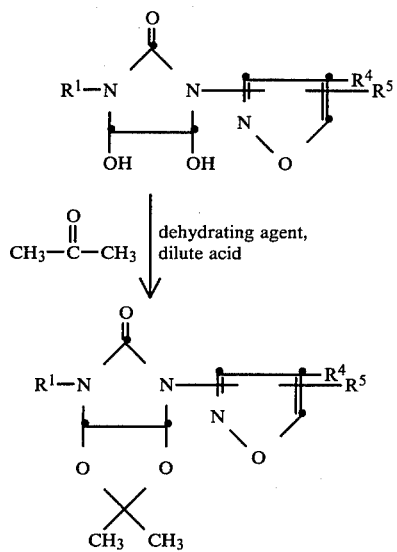

Typical dehydrating agents that can be employed include copper sulfate, sulfuric acid, perchloric acid, zinc chloride, and phosphorus pentoxide. The reaction generally is carried out in the presence of excessive acetone to act as reactant and solvent. The reaction usually is complete within about one to about twenty-four hours when carried out at about 20° to about 50° C. The product is isolated and purified by normal procedures, for example crystallization, chromatography and the like.

Examples of typical classes of isoxazolylimidazolidinones to be employed in the aquatic method of this invention include those listed below:
  A. Those of the formula

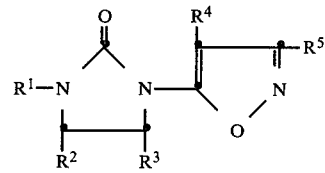

1. $R^1$ is allyl and $R^3$ is hydroxy;
  a. $R^2$ is allyl;
  1a.1. $R^4$ is H and $R^5$ is

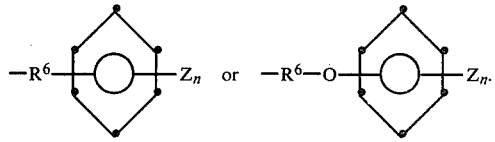

1a.2. $R^4$ is H and $R^5$ is $—R^6—S—R^7$.
  1a.3. $R^4$ is H and $R^5$ is $—R^6—O—R^7$.
  1a.4. $R^4$ is H and $R^5$ is halo-$C_1$-$C_6$ alkyl, preferably trifluoromethyl.
  1.a.5. $R^4$ is H and $R^5$ is $C_3$-$C_7$ cycloalkyl or $C_1$-$C_3$ alkyl-$C_3$-$C_7$ cycloalkyl.
  1a.6. $R^4$ is H and $R^5$ is $C_1$-$C_6$ alkyl.
  1a.7. $R^4$ is H and $R^5$ is tert.-butyl.
  1a.8. $R^4$ is H and $R^5$ is $C_2$-$C_6$ alkenyl.
  1a.9. $R^4$ is H and $R^5$ is $C_2$-$C_6$ alkynyl.
  b. $R^2$ is $C_1$-$C_6$ alkyl.
  1b.1. $R^4$ is H and $R^5$ is

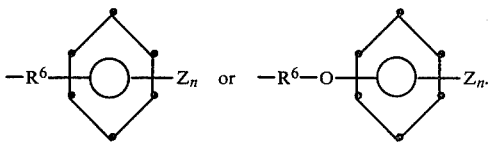

1b.2. $R^4$ is H and $R^5$ is $—R^6—S—R^7$.
  1b.3. $R^4$ is H and $R^5$ is $—R^6—O—R^7$.
  1b.4. $R^4$ is H and $R^5$ is halo-$C_1$-$C_6$ alkyl, preferably trifluoromethyl.
  1b.5. $R^4$ is H and $R^5$ is $C_3$-$C_7$ cycloalkyl or $C_1$-$C_3$ alkyl-$C_3$-$C_7$ cycloalkyl.
  1b.6. $R^4$ is H and $R^5$ is $C_1$-$C_6$ alkyl.
  1b.7. $R^4$ is H and $R^5$ is tert.-butyl.

1b.8. $R^4$ is H and $R^5$ is $C_2$-$C_6$ alkenyl.
1b.9. $R^4$ is H and $R^5$ is $C_2$-$C_6$ alkynyl.
c. $R^2$ is hydroxy.
1c.1. $R^4$ is H and $R^5$ is

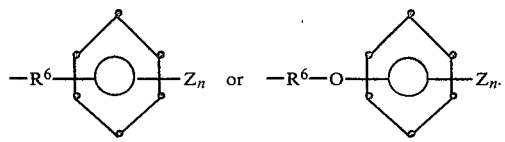

1c.2. $R^4$ is H and $R^5$ is —$R^6$—S—$R^7$.
1c.3. $R^4$ is H and $R^5$ is —$R^6$—O—$R^7$.
1c.4. $R^4$ is H and $R^5$ is halo-$C_1$-$C_6$ alkyl, preferably trifluoromethyl.
1c.5. $R^4$ is H and $R^5$ is $C_3$-$C_7$ cycloalkyl or $C_1$-$C_3$ alkyl-$C_3$-C— cycloalkyl.
1c.6. $R^4$ is H and $R^5$ is $C_1$-$C_6$ alkyl.
1c.7. $R^4$ is H and $R^5$ is tert.-butyl.
1c.8. $R^4$ is H and $R^5$ is $C_2$-$C_6$ alkenyl.
1c.9. $R^4$ is H and $R^5$ is $C_2$-$C_6$ alkynyl.
2. $R^1$ is $C_1$-$C_6$ alkyl and $R^3$ is hydroxy.
a. $R^2$ is allyl;
2a.1. $R^4$ is H and $R^5$ is

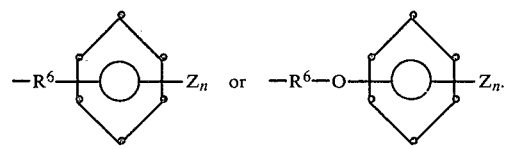

2a.2. $R^4$ is H and $R^5$ is —$R^6$—S—$R^7$.
2a.3. $R^4$ is H and $R^5$ is —$R^6$—O—$R^7$.
2a.4. $R^4$ is H and $R^5$ is halo-$C_1$-$C_6$ alkyl, preferably trifluoromethyl.
2a.5. $R^4$ is H and $R^5$ is $C_3$-$C_7$ cycloalkyl or $C_1$-$C_3$ alkyl-$C_3$-$C_7$ cycloalkyl.
2a.6. $R^4$ is H and $R^5$ is $C_1$-$C_6$ alkyl.
2a.7. $R^4$ is H and $R^5$ is tert.-butyl.
2a.8. $R^4$ is H and $R^5$ is $C_2$-$C_6$ alkenyl.
2a.9. $R^4$ is H and $R^5$ is $C_2$-$C_6$ alkynyl.
b. $R^2$ is $C_1$-$C_6$ alkyl.
2b.1. $R^4$ is H and $R^5$ is

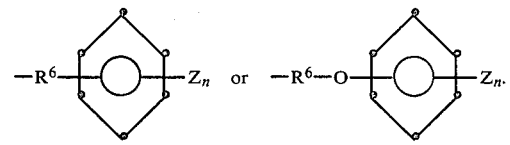

2b.2. $R^4$ is H and $R^5$ is $C_2$-$C_6$ alkenyl.
2b.3. $R^4$ is H and $R^5$ is $C_2$-$C_6$ alkynyl.
c. $R^2$ is hydroxy.
2c.1. $R^4$ is H and $R^5$ is

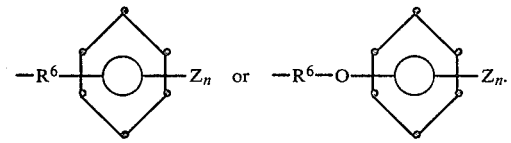

2c.2. $R^4$ is H and $R^5$ is —$R^6$—S—$R^7$.
2c.3. $R^4$ is H and $R^5$ is —$R^6$—O—$R^7$.

2c.4. $R^4$ is H and $R^5$ is halo-$C_1$-$C_6$ alkyl, preferably trifluoromethyl.
2c.5. $R^4$ is H and $R^5$ is $C_3$-$C_7$ cycloalkyl or $C_1$-$C_3$ alkyl-$C_3$-$C_7$ cycloalkyl.
2c.6. $R^4$ is H and $R^5$ is $C_1$-$C_6$ alkyl.
2c.7. $R^4$ is H and $R^5$ is tert.-butyl.
2c.8. $R^4$ is H and $R^5$ is $C_2$-$C_6$ alkenyl.
2c.9. $R^4$ is H and $R^5$ is $C_2$-$C_6$ alkynyl.

B. The most preferred compounds for use in the present aquatic method have the formula:

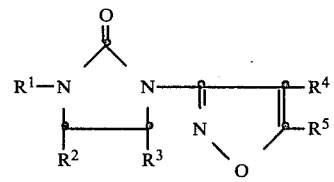

1. $R^1$ is allyl and $R^3$ is hydroxy;
a. $R^2$ is allyl;
1a.1. $R^4$ is H and $R^5$ is

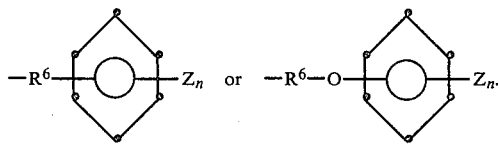

1a.2. $R^4$ is H and $R^5$ is —$R^6$—S—$R^7$.
1a.3. $R^4$ is H and $R^5$ is —$R^6$—O—$R^7$.
1a.4. $R^4$ is H and $R^5$ is halo-$C_1$-$C_6$ alkyl, preferably trifluoromethyl.
1a.5. $R^4$ is H and $R^5$ is $C_3$-$C_7$ cycloalkyl or $C_1$-$C_3$ alkyl-$C_3$-$C_7$ cycloalkyl.
1a.6. $R^4$ is H and $R^5$ is $C_1$-$C_6$ alkyl.
1a.7. $R^4$ is H and $R^5$ is tert.-butyl.
1a.8. $R^4$ is H and $R^5$ is $C_2$-$C_6$ alkenyl.
1a.9. $R^4$ is H and $R^5$ is $C_2$-$C_6$ alkynyl.
b. $R^2$ is $C_1$-$C_6$ alkyl.
1b.1. $R^4$ is H and $R^5$ is

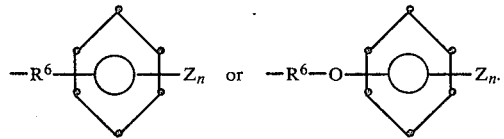

1b.2. $R^4$ is H and $R^5$ is —$R^6$—S—$R^7$.
1b.3. $R^4$ is H and $R^5$ is —$R^6$—O—$R^7$.
1b.4. $R^4$ is H and $R^5$ is halo-$C_1$-$C_6$ alkyl, preferably trifluoromethyl.
1b.5. $R^4$ is H and $R^5$ is $C_3$-$C_7$ cycloalkyl or $C_1$-$C_3$ alkyl-$C_3$-$C_7$ cycloalkyl.
1b.6. $R^4$ is H and $R^5$ is $C_1$-$C_6$ alkyl.
1b.7. $R^4$ is H and $R^5$ is tert.-butyl.
1b.8. $R^4$ is H and $R^5$ is $C_2$-$C_6$ alkenyl.
1b.9. $R^4$ is H and $R^5$ is $C_2$-$C_6$ alkynyl.
c. $R^2$ is hydroxy.
1c.1. $R^4$ is H and $R^5$ is

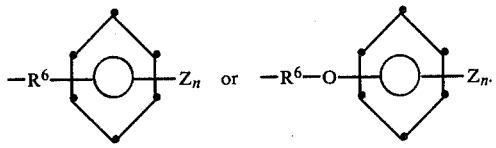

1c.2. $R^4$ is H and $R^5$ is —$R^6$—S—$R^7$.
1c.3. $R^4$ is H and $R^5$ is —$R^6$—O—$R^7$.
1c.4. $R^4$ is H and $R^5$ is halo-$C_1$-$C_6$ alkyl, preferably trifluoromethyl.
1c.5. $R^4$ is H and $R^5$ is $C_3$-$C_7$ cycloalkyl or $C_1$-$C_3$ alkyl-$C_3$-$C_7$ cycloalkyl.
1c.6. $R^4$ is H and $R^5$ is $C_1$-$C_6$ alkyl.
1c.7. $R^4$ is H and $R^5$ is tert.-butyl.
1c.8. $R^4$ is H and $R^5$ is $C_2$-$C_6$ alkenyl.
1c.9. $R^4$ is H and $R^5$ is $C_2$-$C_6$ alkynyl.
2. $R^1$ is $C_1$-$C_6$ alkyl and $R^3$ is hydroxy.
a. $R^2$ is allyl;
2a.1. $R^4$ is H and $R^5$ is

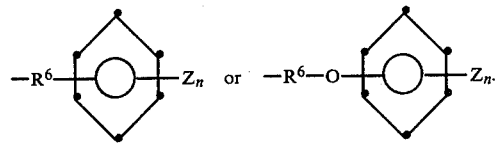

2a.2. $R^4$ is H and $R^5$ is —$R^6$—S—$R^7$.
2a.3. $R^4$ is H and $R^5$ is —$R^6$—O—$R^7$.
2a.4. $R^4$ is H and $R^5$ is halo —$C_1$-$C_6$ alkyl, preferably trifluoromethyl.
2a.5. $R^4$ is H and $R^5$ is $C_3$-$C_7$ cycloalkyl or $C_1$-$C_3$ alkyl-$C_3$-$C_7$ cycloalkyl.
2a.6. $R^4$ is H and $R^5$ is $C_1$-$C_6$ alkyl.
2a.7. $R^4$ is H and $R^5$ is tert.-butyl.
2a.8. $R^4$ is H and $R^5$ is $C_2$-$C_6$ alkenyl.
2a.9. $R^4$ is H and $R^5$ is $C_2$-$C_6$ alkynyl.
b. $R^2$ is $C_1$-$C_6$ alkyl.
2b.1. $R^4$ is H and $R^5$ is

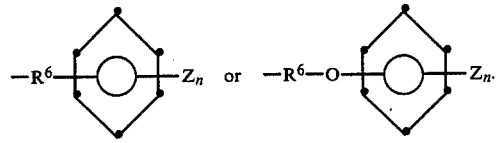

2b.2. $R^4$ is H and $R^5$ is $C_2$-$C_6$ alkenyl.
2b.3. $R^4$ is H and $R^5$ is $C_2$-$C_6$ alkynyl.
c. $R^2$ is hydroxy.
2c.1. $R^4$ is H and $R^5$ is

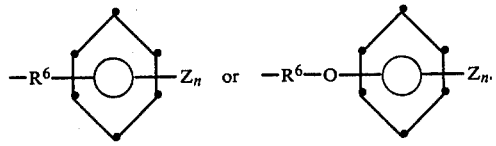

2c.2. $R^4$ is H and $R^5$ is —$R^6$—S—$R^7$.
2c.3. $R^4$ is H and $R^5$ is —$R^6$—O—$R^7$.
2c.4. $R^4$ is H and $R^5$ is halo —$C_1$-$C_6$ alkyl, preferably trifluoromethyl.
2c.5. $R^4$ is H and $R^5$ is $C_3$-$C_7$ cycloalkyl or $C_1$-$C_3$ alkyl-$C_3$-$C_7$ cycloalkyl.
2c.6. $R^4$ is H and $R^5$ is $C_1$-$C_6$ alkyl.
2c.7. $R^4$ is H and $R^5$ is tert.-butyl.
2c.8. $R^4$ is H and $R^5$ is $C_2$-$C_6$ alkenyl.
2c.9. $R^4$ is H and $R^5$ is $C_2$-$C_6$ alkynyl.

Compounds specifically provided by this invention as new compositions of matter are defined by the formula

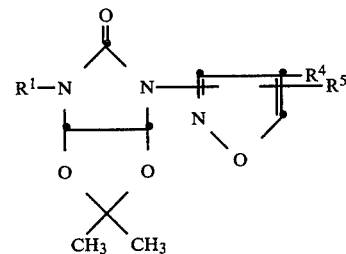

wherein $R^1$, $R^4$ and $R^5$ are as defined above. Exemplary of these new acetonide isoxazolylimidazolidinones are the following:

C. Those of the formula

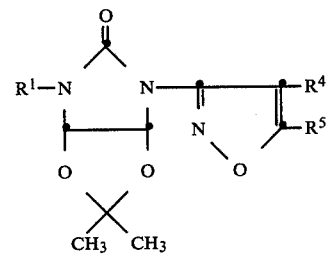

1. $R^1$ is allyl.
a. $R^4$ is hydrogen.
1a.1. $R^5$ is

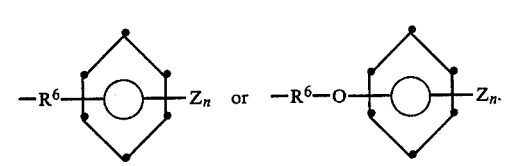

1a.2. $R^5$ is —$R^6$—S—$R^7$.
1a.3. $R^5$ is —$R^6$—O—$R^7$.
1a.4. $R^5$ is halo-$C_1$-$C_6$ alkyl, preferably trifluoromethyl, for example:
3-(5-trifluoromethyl-3-isoxazolyl)-1-allyl-4,5-dihydroxy-2-imidazolidinone acetonide.
1a.5. $R^5$ is $C_3$-$C_7$ cycloalkyl or $C_1$-$C_3$ alkyl-$C_3$-$C_7$ cycloalkyl;
3-(5-cyclohexyl-3-isoxazolyl)-1-allyl-4,5-dihydroxy-2-imidazolidinone acetonide;
3-[5-(1-ethylcyclohexyl)-3-isoxazolyl]-1-allyl-4,5-dihydroxy-2-imidazolidinone acetonide.
1a.6. $R^5$ is $C_1$-$C_6$ alkyl.
3-(5-isopropyl-3-isoxazolyl)-1-allyl-4,5-dihydroxy-2-imidazolidinone acetonide.
1a.7. $R^5$ is tert.-butyl.
3-(5-tert.-butyl-3-isoxazolyl-1-allyl-4,5-dihydroxy-2-imidazolidinone acetonide.
1a.8. $R^5$ is $C_2$-$C_6$ alkenyl.
1a.9. $R^5$ is $C_2$-$C_6$ alkynyl.
2. $R^1$ is $C_1$-$C_6$ alkyl.

a. R⁴ is hydrogen.
2a.1. R⁵ is

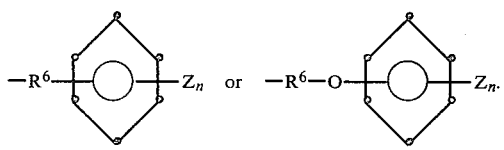

2a.2. R⁵ is —R⁶—S—R⁷.
2a.3. R⁵ is —R⁶—O—R⁷.
2a.4. R⁵ is halo-$C_1$-$C_6$ alkyl, preferably trifluoromethyl.
3-(5-trifluoromethyl-3-isoxazolyl)-1-methyl-4,5-dihydroxy-2-imidazolidinone acetonide.
2a.5. R⁵ is $C_3$-$C_7$ cycloalkyl or $C_1$-$C_3$ alkyl-$C_3$-$C_7$ cycloalkyl.
3-(5-cyclopentyl-3-isoxazolyl)-1-ethyl-4,5-dihydroxy-2-imidazolidinone acetonide.
3-[5-(1-methylcycloheptyl)-3-isoxazolyl]-1-methyl-4,5-dihydroxy-2-imidazolidinone acetonide.
2a.6. R⁵ is $C_1$-$C_6$ alkyl.
3-(5-isopropyl-3-isoxazolyl)-1-methyl-4,5-dihydroxy-2-imidazolidinone acetonide.
2a.7. R⁵ is tert.-butyl.
3-(5-tert.-butyl-3-isoxazolyl)-1-methyl-4,5-dihydroxy-2-imidazolidinone acetonide.
2a.8. R⁵ is $C_2$-$C_6$ alkenyl.
2a.9. R⁵ is $C_2$-$C_6$ alkynyl.
D. Those of the formula

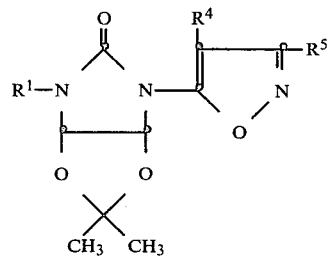

1. R¹ is allyl.
a. R⁴ is hydrogen.
1a.1. R⁵ is

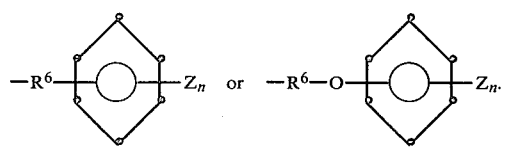

1a.2. R⁵ is —R⁶—S—R⁷.
3-(3-methylthiomethyl-5-isoxazolyl)-1-allyl-4,5-dihydroxy-2-imidazolidinone acetonide.
1a.3. R⁵ is —R⁶—O—R⁷.
1a.4. R⁵ is halo-$C_1$-$C_6$ alkyl, preferably trifluoromethyl.
3-(3-trifluoromethyl-5-isoxazolyl)-1-allyl-4,5-dihydroxy-2-imidazolidinone acetonide.
1a.5. R⁵ is $C_3$-$C_7$ cycloalkyl or $C_1$-$C_3$ alkyl-$C_3$-$C_7$ cycloalkyl.
3-(3-cyclopropyl-5-isoxazolyl)-1-allyl-4,5-dihydroxy-2-imidazolidinone acetonide.
1a.6. R⁵ is $C_1$-$C_6$ alkyl.
3-[3-(1-ethyl-1-methylpropyl)-5-isoxazolyl]-1-allyl-3,4-dihydroxy-2-imidazolidinone acetonide.
1a.7. R⁵ is tert.-butyl.
3-(3-tert.butyl-5-isoxazolyl)-1-allyl-4,5-dihydroxy-2-imidazolidinone acetonide.
1a.8. R⁵ is $C_2$14 $C_6$ alkenyl.
1a.9. R⁵ is $C_2$-$C_5$ alkynyl.
2. R¹ is $C_1$-$C_6$ alkyl.
a. R⁴ is hydrogen.
2a.1. R⁵ is

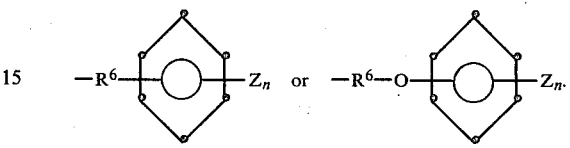

2a.2. R⁵ is —R⁶—S—R⁷.
2a.3. R⁵ is —R⁶—O—R⁷.
3-[3-(1,1-dimethylmethoxymethyl)-5-isoxazolyl]-1-methyl-4,5-dihydroxy-2-imidazolidinone acetonide.
2a.4. R⁵ is halo-$C_1$-$C_6$ alkyl, preferably trifluoromethyl.
3-(3-trifluoromethyl-5-isoxazolyl)-1-methyl-4,5-dihydroxy-2-imidazolidinone acetonide.
2a.5. R⁵ is $C_3$-$C_7$ cycloalkyl or $C_1$-$C_3$ alkyl-$C_3$-$C_7$ cycloalkyl.
3-[3-(1-ethylcyclohexyl)-5-isoxazolyl]-1-ethyl-4,5-dihydroxy-2-imidazolidinone acetonide.
2a.6. R⁵ is $C_1$-$C_6$ alkyl.
3-(3-isopropyl-5-isoxazolyl)-1-methyl-4,5-dihydroxy-2-imidazolidinone acetonide.
2a.7. R⁵ is tert.-butyl.
3-(3-tert.-butyl-5-isoxazolyl)-1-methyl-4,5-dihydroxy-2-imidazolidinone acetonide.
2a.8. R⁵ is $C_2$-$C_6$ alkenyl.
2a.9. R⁵ is $C_2$-$C_6$ alkynyl.
3-[3-(2-butynyl)-5-isoxazolyl]-1-methyl-4,5-dihydroxy-2-imidazolidinone acetonide.

The synthesis of compounds defined herein is more fully illustrated by the following working examples.

EXAMPLE 1

3-[5-(1,1-dimethylethyl)-3-isoxazolyl]-4,5-dihydroxy-1-methyl-2-imidazolidinone

A solution of 14 grams of 40% (v/v) glyoxal/water was diluted with 1.0% aqueous sodium hydroxide to pH 7–8. This glyoxal/water solution was then added in one portion to a solution of 3.4 g. of 1-[5-(1,1-dimethylethyl)-3-isoxazolyl]-3-methylurea in 120 ml. of ethanol. The reaction mixture was heated to reflux for one hour, and the solvent was then removed by evaporation to provide 12.0 grams of yellow oil. The oil was dissolved in diethyl ether and heated, and then the mixture was filtered to remove a small amount of insoluble material. The solvent was removed from the filtrate to afford 11 grams of oil. The oil was dissolved in dichloromethane and washed with water. Evaporation of the organic solvent provided 4.0 grams of a white foam identified as 3-[5-(1,1-dimethylethyl)-3-isoxazolyl]-4,5-dihydroxy-1-methyl-2-imidazolidinone. Mass Spectrum M⁺ Theory 255, Found 255.

EXAMPLE 2

3-[5-(1,1-dimethylethyl)-3-isoxazolyl]-4,5-dihydroxy-1-methyl-2-imidazolidinone acetonide To a solution of 1.0 gram of 3-[5-(1,1-dimethylethyl)-3-isoxazolyl]-4,5-dihydroxy-1-methyl-2-imidazolidinone in 20 ml. of anhydrous acetone were added three drops of 70% perchloric acid. The reaction mixture stood at ambient temperature for sixteen hours, and then was diluted with 100 ml. of water. The white crystalline precipitate was collected by filtration and recrystallized from diethyl ether and hexane to afford 3-[5-(1,1-dimethylethyl)-3-isoxazolyl]-4,5-dihydroxy-1-methyl-2-imidazolidinone acetonide. M.P. 157°–159° C. Mass Spectrum M+ Theory 295; Found 295.

Analysis calculated for $C_{14}H_{21}N_3O_4$ Theory: C, 56.94; H, 7.17; N, 14.23. Found: C, 56.65; H, 7.43; N, 13.96.

The aquatic method provided by this invention permits the control and elimination of aquatic weeds employing a compound defined herein. The invention contemplates the control and elimination of all forms of plant life that infests ponds, lakes, water ways, water reservoirs, including water towers and containers employed in the storage of water for human consumption. The invention thus provides a method for controlling algae and aquatic plant growth including submersed, floating, emergent and ditchbank vegetation. Because the compounds are useful in control aquatic plant life, an important embodiment of this invention is a method of use employing the compounds.

The novel compounds provided by this invention, with potent aquatic herbicides, also have some terrestrial herbicidal activity. The pre-emergent and post-emergent terrestrial herbicidal activity of typical isoxazolylimidazolidinone acetonides of this invention has been determined in standard greenhouse experiments. Such experiments were carried out by first formulating a test compound for convenient soil surface or overtop foliar spray application. The test compound was formulated by dissolving 0.2 percent by weight in a solution containing 4.0 percent by weight acetone, 4.0 percent by weight ethanol, and 91.7 percent by weight of deionized water, and 0.1 percent by weight of a commercial surfactant, for example Toximul R and S, which are blends of anionic and nonionic surface active agents (Stepan Chemical Co. Northfield, Ill., 60093). The solution containing the test compound was then serially diluted with deionized water to the appropriate volume containing the desired concentration of test compound. The formulated compounds were applied pre-emergence and/or post-emergence to metal greenhouse flats filled with soil and seeded to test plants. The compounds were evaluated at several application rates, initially at 15 pounds per acre (16.8 kg/ha) and at lower rates until compound activity diminished. Pre-emergence applications were made to the soil surface of the seeded flats. Post-emergence applications were made to the foliage of the various plant species approximately twelve days after seeding. All treated flats were maintained in a greenhouse following treatment. Evaluations of compound activity were made in the form of plant injury rating on a scale of 1 to 5. The rating of "1" refers to no plant injury; "2" slight injury; "3" moderate injury; "4" severe injury; and "5" death to all treated plants. Evaluations were made from 11 to 14 days after post-emergence application, and from 18 to 21 days following pre-emergence application.

Table 1 which follows presents the herbicidal activity of a compound provided by this invention.

TABLE 1

Plant Injury Ratings for the Compound of Example 2

| PLANT SPECIES | appln. rate lbs/A (kg/ha) | | | | |
|---|---|---|---|---|---|
| | 15 | 8 | 4 | 2 | 1 |
| Pre-emergence | | | | | |
| Corn | | | | | |
| Cotton | | | | | |
| Soybean | | | | | |
| Wheat | | | | | |
| Alfalfa | | | | | |
| Sugar Beet | | | | | |
| Rice | | | | | |
| Cucumber | | | | | |
| Tomato | 1 | 1 | | | |
| Barnyard Grass | | 1 | | | |
| Lambsquarter | | | | | |
| Large Crabgrass | 1 | 2 | | | |
| Mustard | | 1 | | | |
| Pigweed | 1 | 4 | | | |
| Foxtail | | 3 | | | |
| Wildoat | | 1 | | | |
| Velvetleaf | | 3 | | | |
| Jimsonweed | | | | | |
| Morningglory | | 2 | | | |
| Zinnia | | 1 | | | |
| Post-emergence | | | | | |
| Tomato | 3 | 1 | 2 | 1 | 1 |
| Large Crabgrass | 3 | 2 | 3 | 1 | 1 |
| Pigweed | 5 | 5 | 5 | 3 | 2 |
| Foxtail | | 2 | 3 | 3 | 1 |
| Velvetleaf | | 2 | 4 | 2 | 1 |
| Morningglory | | 2 | 2 | 2 | 1 |
| Zinnia | | 3 | 2 | 1 | 1 |
| Wildoat | | 1 | 1 | 1 | 1 |

The compounds defined by this invention are particularly useful as aquatic algicides, aquatic growth regulators and aquatic herbicides. A preferred embodiment of this invention is a method for controlling aquatic plant growth which comprises applying an aquatic herbicidally effective amount of a compound as defined herein to the aquatic plants to be controlled or to the water in which the plants are growing.

The compounds of the invention have been evaluated in a standard aquatic algicide test designed to show algicidal activity. In a primary screen, the compounds were evaluated against *Chlorella vulgaris*, *Scenedesmus quadricanda*, and *Anacystis nidulans*. These algae species were grown on agar slants containing artificial media (Hughes' media). The agar slants were employed in the inoculation of the test media, which itself is an aqueous Hughes' media. Five milliliters of sterile Hughes' media is used to wash the agar slants, and this is then added to 400 ml. of sterile Hughes' media. Two milliliters of the inoculated media is then added to each of several 12 ml. disposable vials.

The test compounds are formulated for evaluation by dissolving 10 mg. of compound in a solution of 0.5 ml. acetone and 4.5 ml. of sterile 0.1% aqueous polyoxyethylene sorbitan monooleate (Tween 80). Aliquot portions of the formulated test compounds are then added to the vials containing the various algae species. Visual observations and comparisons to non-treated control vials were made 7 days after treatment. Activity ratings were made on a scale of 1 to 5 according to the following meanings:

1 = no effect
2 = slight effect
3 = moderate effect
4 = heavy effect
5 = 100% control.

Table 2 which follows presents the algicidal activity of compounds of the invention evaluated according to the foregoing procedure.

TABLE 2

Aquatic Algicide Activity

| Compound of Example No. | Concentration ppm | Control Ratings | | | |
|---|---|---|---|---|---|
| | | Chlorella vulgaris | Scenedesmus quadricanda | Anacystis nidulans | Anabaena |
| Control | | 0 | 0 | 0 | 0 |
| 2 | 10 | 5 | 5 | 5 | 1 |

As noted above, the compounds of this invention also have activity in the regulation of aquatic plant growth and are useful as aquatic herbicides. The following method was used in the laboratory to evaluate the aquatic growth regulating properties of the compounds disclosed herein.

The compounds for this test were formulated in the following manner. Twenty milligrams of compound was weighed into a 12 ml. disposable vial. To the vial containing the compound were added 1 ml. of acetone and 9 ml. of aqueous 0.1 percent polyoxyethylene sorbitan monooleate (Tween 80). This solution was then diluted with appropriate volumes of water to obtain solutions containing 10, 1, 0.5 and 0.25 ppm (parts per million) of test compound.

Terminal pieces of Florida elodea, *Hydrilla verticillata* (L.F.), (hereinafter identified as hydrilla) 10 cm. long, without branching, were prepared for testing. Three such cuttings were placed in each plastic container holding 785 ml. of water containing the formulated test compound and 3 ml. of Hoagland's nutrient solution. Three 10 cm. cuttings of hydrilla were placed in each of several control containers of water. To the water in each control container there was also added the amount of solvent used to formulate the test compound for each container.

After a period of two to three weeks, measurements were made to determine the total length of each plant. An average total growth was obtained by dividing the total combined lengths by the number of replicates. By subtracting 10 cm. from the average total length, the average increase in growth was obtained. This difference was divided by the average increase in length of the plants in the solvent controls (SC) and the quotient multiplied by 100 to give a percent inhibition.

$$\frac{\text{Total combined length of Replicates}}{\text{Number of Replicates}} = \text{Average Length}$$

Avg. Length - 10 cm. = Avg. Increased Growth $$\frac{\text{Avg. Increased Growth}}{\text{Avg. Increased Growth } SC} \times 100 = \% \text{ Inhibition}$$

Several of the compounds of the invention were evaluated further as aquatic herbicides by employing additional weed species. The compounds were formulated for evaluation as described above, and the herbicidal activity was determined by visual observations based upon non-treated controls. Activity ratings were made on a scale of 1 to 5 as follows:

| | |
|---|---|
| 1 | = no observable effect |
| 2 | = slight plant injury |
| 3 | = moderate plant injury |
| 4 | = 50–90% plant injury |
| 5 | = plants completely killed |
| A = abscission | D = stem disintegration |
| C = chlorosis | N = necrosis |

The results of this test are reported in Tables 3 and 4 which follow.

TABLE 3

Aquatic Herbicide Activity 3-weeks post-treatment

| Compound of Example No. | Concentration ppm | Hydrilla | Coontail | Duckweed |
|---|---|---|---|---|
| Control | | 1 | 1 | 1 |
| 1 | 10 | 4D/2D | 1/1 | 5C/5C |
| | 4 | 1/2N | 1/2C | 4C/3C |
| | 2 | 1/1 | 1/2C | 1/2C |
| 2 | 4 | 1/1 | 1/1 | 1/1 |
| | 2 | 2N/2N | 2C/1 | 1/1 |

TABLE 4

Aquatic Herbicide Activity

| | Compound of Example No. | | Concentration ppm | |
|---|---|---|---|---|
| | Control | 2 | 2 | 1 | 0.5 |
| 1-week post treatment | | | | | |
| Hydrilla | 1 | 1 | 1 | 1 | 1 |
| Coontail | 1 | 1 | 1 | 1 | 1 |
| Duckweed | 1 | 2C | 2C | 1 | 1 |
| S. Naiad | 1 | 3C | 3C | 1 | 1 |
| Eurasian Milfoil | 1 | 3C | 3C | 1 | 1 |
| Cabomba | 1 | 2C | 2C | 2C | 1 |
| Sago Pond Weed | 1 | 1 | 1 | 1 | 1 |
| 2-week post treatment | | | | | |
| Hydrilla | 1 | 1 | 1 | 1 | 1 |
| Coontail | 1 | 3C | 3C | 2C | 2C |
| Duckweed | 1 | 1 | 1 | 1 | 1 |
| S. Naiad | 1 | 3D | 3D | 3C | 1 |
| Eurasian Milfoil | 1 | 2N | 2N | 1 | 1 |
| Cabomba | 1 | 2C | 2C | 3C | 1 |
| Sago Pond Weed | 1 | 2N | 2N | 1 | 4C |
| 3-week post treatment | | | | | |
| Hydrilla | 1 | 1 | 1 | 1 | 1 |
| Coontail | 1 | 3C | 3C | 3C | 3C |
| Duckweed | 1 | 1 | 1 | 1 | 1 |
| S. Naiad | 1 | 3D | 3D | 1 | 2D |
| Eurasian Milfoil | 1 | 3D | 3D | 1 | 2C |
| Cabomba | 1 | 2C | 2C | 2A | 3C |
| Sago Pond Weed | 1 | 2C | 2C | 1 | 4C |

The compounds of the invention are also expected to be useful in the control of water hyacinth. Water hyacinth is a floating aquatic plant of the order *Eichhornia crassipes* of the family Pontederiaceae. The plant is very troublesome in warm regions since it floats on water and often clogs waterways, and is very difficult to control safely.

As the data presented in the Tables above demonstrate, the compounds defined herein are useful in the control of aquatic vegetative growth. A preferred embodiment of this invention is a method of eliminating and controlling the growth of aquatic plants. This method is practiced by adding the active isoxazolylimidazolidinone derivatives to the water containing the submerged, emergent, ditchbank or floating aquatic plants, or otherwise contacting the plants with the active compounds, for example, by applying the compounds to the sub-aqueous soil in which the aquatic plants are rooted. The compounds may be applied to the water as dusts when admixed with a powdered solid carrier such as bentonite, Fuller's earth, diatomaceous earth, or various mineral silicates, e.g., mica, talc, pyrophyllite, and clays. The compounds may also be mixed with surface-active dispersing agents to form concentrates to facilitate dispersion in water and to improve the wetting properties when used as sprays. If desired, the compounds may be mixed with a powdered solid carrier, together with a surface-active dispersing agent, so that a wettable powder may be obtained which may be applied directly, or which may be shaken with water to make an aqueous dispersion for application in that form. These wettable powder formulations suitably contain from about 25 to about 85 percent by weight of the active ingredient, i.e., an aquatic growth regulating compound coming within the scope of the generic formulae, supra. The compounds may be dissolved in an oil, such as a hydrocarbon or chlorinated hydrocarbon oil, and the oil solution of the compound dispersed in water with the aid of a surface-active dispersing agent to give a sprayable aqueous dispersion. Such surface-active dispersing agents may be anionic, nonionic, or cationic surface-active agents. Such surface-active agents are well-known, and reference is made to Hoffman et al., U.S. Pat. No. 2,614,916, columns 2–4, for detailed examples of the same. The compounds useful in this embodiment of the invention may also be applied by the aerosol method. Solutions for the aerosol treatment may be prepared by dissolving the compound directly in the aerosol carrier, which is a liquid under pressure, but which is a gas at ordinary temperature (e.g. 20° C.) and atmospheric pressure; or, the aerosol solution may be prepared by first dissolving the compound in a less volatile solvent, and then admixing such solution with the highly volatile liquid aerosol carrier.

Further, the compounds useful as aquatic growth regulators can also be applied in an invert emulsion formulation. An invert emulsion formulation is prepared by first making a solution of an aquatic growth regulating compound in heavy oils, such as diesel fuel, inverting oil, and the like, and combining the thus-obtained solution with water under high shear stirring. The thick emulsion is placed in the water and sinks to the bottom of the lake, river, pond, or the like, and the aquatic growth regulator is gradually released to control the growth of the aquatic plants. The following is an example of an invert emulsion formulation, prepared using the compound of Example No. 2 of this application.

| Invert Emulsion | |
|---|---|
| Compound of Example No. 2 | 12.5 gm |
| Diesel Fuel | 333 ml |
| Inverting oil* | 333 ml |

*Vioko-Rhap Inverting Oil (Rhodia, Inc.)

Two-hundred fifty milliliters of this solution is combined with 3750 ml. of water under high shear stirring to give a thick invert emulsion.

The compounds useful as aquatic growth regulators can also be applied as pellets which are prepared from a mixture of about 5% of the active ingredient, about 85% clay, and about 10% water, all percentages being by weight. The mixture is then extruded through a pellet mill using a suitably sized die, e.g., about ⅛ in. diameter. The extruded pellets are about ⅛ in. by 1½ in., and are then dried to about 8% moisture content.

The method of controlling aquatic plant growth provided by this invention is practiced by adding to the water containing the submerged or floating plants a growth-regulating or herbicidal amount of one of the herein-disclosed compounds, such that a concentration of from about 0.01 to about 10 ppm. of the active compound is attained. A preferred method of aquatic plant growth regulation provided by this invention is directed toward the control of plants such as water hyacinth. Such plants can be controlled by foliar or root application of a compound of this invention at a rate of about 0.01 to about 1.0 pounds per acre (about 0.011 to about 1.1 kg/ha).

The optimum concentration of active compound for any specific aquatic weed control problem varies with the temperature, the species to be controlled, and the shape of the body of water to be treated. At higher water temperatures, less compound is generally required for a given degree of control than is needed at lower temperatures. When used to control algae or aquatic plant growth, the compounds will usually be employed at concentrations of about 0.1 to about 10 ppm. In terms of pounds of compound per acre of water one foot deep, 0.1 to 10 ppm. is equal to about 0.3 to about 30 pounds per acre of water one foot deep.

We claim:

1. A method for controlling the growth of aquatic plants comprising contacting the plants or the water in which the plants are growing with an aquatic herbicidally-effective amount of a compound of the formula:

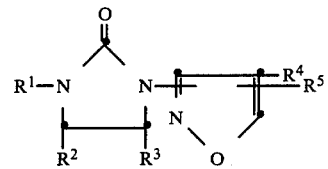

wherein:
$R^1$ is $C_1$–$C_6$ alkyl or allyl;
$R^2$ is hydrogen, $C_1$–$C_6$ alkyl, allyl, or hydroxy;
$R^3$ is hydroxy or halo;
$R^4$ is hydrogen, $C_1$–$C_6$ alkyl, halo, cyano, or nitro;
$R^5$ is $C_1$–$C_6$ alkyl, $C_2$–$C_6$ alkenyl, $C_2$–$C_6$ alkynyl, $C_3$–$C_7$ cycloalkyl, $C_1$–$C_3$alkyl-$C_3$–$C_7$ cycloalkyl, halo-$C_1$–$C_6$ alkyl, —$R^6$—O—$R^7$ or —$R^6$—S—$R^7$, where $R^6$ is $C_1$–$C_6$ alkylene and $R^7$ is $C_1$–$C_6$ alkyl; or $R^5$ is

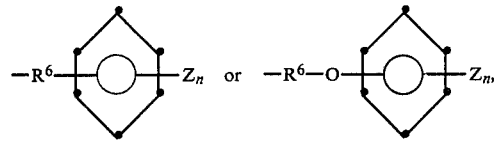

wherein:
Z is nitro, halo, or $R^7$, and n is 0, 1, 2 or 3;
provided that $R^2$ is allyl or hydroxy when $R^1$ is allyl, $R^3$ is hydroxy, and $R^5$ is alkyl, cycloalkyl, alkylcycloalkyl or haloalkyl.

2. The method of claim 1 employing a compound wherein $R^4$ is hydrogen.

3. The method of claim 2 employing a compound wherein $R^3$ is hydroxy.

4. The method of claim 3 employing a compound wherein $R^2$ is hydroxy.

5. The method of claim 4 employing a compound wherein $R^1$ is $C_1$-$C_6$ alkyl.

6. The method of claim 5 employing a compound wherein $R^1$ is methyl.

7. The method of claim 6 employing a compound wherein $R^5$ is halo-$C_1$-$C_6$ alkyl.

8. The method of claim 7 employing a compound wherein $R^5$ is trifluoromethyl.

9. The method of claim 6 employing a compound wherein $R^5$ is $C_1$-$C_6$ alkyl.

10. The method of claim 9 employing a compound wherein $R^5$ is tert.-butyl.

11. The method of claim 10 employing a 3-(3-tert.-butyl-5-isoxazolyl)-1-methyl-4,5-dihydroxy-2-imidazolidinone.

12. The method of claim 10 employing 3-(5-tert.-butyl-3-isoxazolyl)-1-methyl-4,5-dihydroxy-2-imidazolidinone.

13. The method of claim 9 employing a compound wherein $R^5$ is isopropyl.

14. The method of claim 13 employing a 3-(5-isopropyl-3-isoxazolyl)-1-methyl-4,5-dihydroxy-2-imidazolidinone.

15. The method of claim 13 employing a 3-(3-isopropyl-5-isoxazolyl)-1-methyl-4,5-dihydroxy-2-imidazolidinone.

16. An aquatic formulation comprising an isoxazolylimidazolidinone as defined in claim 1 together with an aquatically-acceptable carrier.

17. The formulation of claim 16 wherein the active ingredient is a compound of the formula

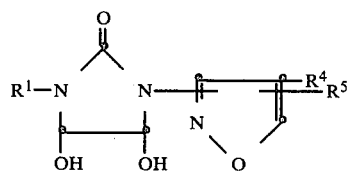

wherein:
$R^1$ is $C_1$-$C_6$ alkyl or allyl;
$R^4$ is hydrogen, $C_1$-$C_6$ alkyl, halo, cyano, or nitro;
$R^5$ is $C_1$-$C_6$ alkyl, $C_2$-$C_6$ alkenyl, $C_2$-$C_6$ alkynyl, $C_3$-$C_7$ cycloalkyl, $C_1$-$C_3$ alkyl-$C_3$-$C_7$ cycloalkyl, halo-$C_1$-$C_6$ alkyl, —$R^6$—O—$R^7$ or —$R^6$—S—$R^7$, where $R^6$ is $C_1$-$C_6$ alkylene and $R^7$ is $C_1$-$C_6$ alkyl; or $R^5$ is

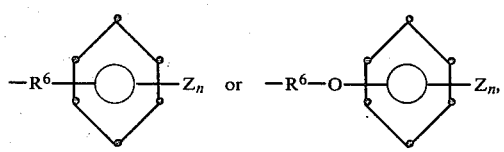

wherein: Z is nitro, halo, or $R^7$, and n is 0, 1, 2 or 3.

18. The formulation of claim 17 wherein $R^1$ is alkyl.

19. The formulation of claim 18 wherein $R^4$ is hydrogen.

20. The formulation of claim 19 wherein $R^5$ is $C_1$-$C_6$ alkyl.

21. The formulation of claim 20 wherein $R^5$ is tert.-butyl.

22. The formulation of claim 20 wherein $R^5$ is iso-propyl.

23. The formulation of claim 19 wherein $R^5$ is halo-$C_1$-$C_6$ alkyl.

24. The formulation of claim 23 wherein $R^5$ is trifluoromethyl.

* * * * *